(12) United States Patent
Fechner et al.

(10) Patent No.: US 7,709,027 B2
(45) Date of Patent: *May 4, 2010

(54) ANTIMICROBIAL, ANTI-INFLAMMATORY, WOUND-HEALING GLASS POWDER AND USE THEREOF

(75) Inventors: Jörg Hinrich Fechner, Mainz (DE); José Zimmer, Ingelheim (DE)

(73) Assignee: Schott AG, Mainz (DE)

( * ) Notice: Subject to any disclaimer, the term of this patent is extended or adjusted under 35 U.S.C. 154(b) by 78 days.

This patent is subject to a terminal disclaimer.

(21) Appl. No.: 10/487,187

(22) PCT Filed: Aug. 17, 2002

(86) PCT No.: PCT/EP02/09220

§ 371 (c)(1),
(2), (4) Date: Mar. 24, 2004

(87) PCT Pub. No.: WO03/018496

PCT Pub. Date: Mar. 6, 2003

(65) Prior Publication Data

US 2004/0253321 A1    Dec. 16, 2004

(30) Foreign Application Priority Data

| Aug. 22, 2001 | (DE) | 101 41 116 |
| Nov. 20, 2001 | (DE) | 101 56 577 |
| Mar. 27, 2002 | (DE) | 102 13 630 |
| Mar. 27, 2002 | (DE) | 102 13 632 |

(51) Int. Cl.
| A61K 9/14  | (2006.01) |
| A61K 8/00  | (2006.01) |
| A61K 8/02  | (2006.01) |
| A61K 8/18  | (2006.01) |
| A61K 8/25  | (2006.01) |
| A61K 8/26  | (2006.01) |
| A61K 8/27  | (2006.01) |
| A61K 8/21  | (2006.01) |
| A61K 33/06 | (2006.01) |
| A61K 33/16 | (2006.01) |
| A61K 33/22 | (2006.01) |
| A61K 33/30 | (2006.01) |

(52) U.S. Cl. ............ 424/489; 424/65; 424/67; 424/68; 424/401; 424/659; 424/660; 424/673; 424/691; 424/724

(58) Field of Classification Search .......... 424/65, 424/401, 439, 489, 67, 68, 659, 660, 673, 424/691, 724

See application file for complete search history.

(56) References Cited

U.S. PATENT DOCUMENTS

| 3,785,835 A | 1/1974 | Izumitani et al. | |
| 3,798,041 A | 3/1974 | Izumitani et al. | |
| 3,926,246 A | 12/1975 | Corbett et al. | 164/56 |
| 4,092,139 A | 5/1978 | Ference | 65/30 R |
| 5,022,921 A | 6/1991 | Aitken | |
| 5,034,353 A | 7/1991 | Shibuya et al. | 501/3 |
| 5,074,916 A | 12/1991 | Hench et al. | 106/35 |
| 5,196,381 A | 3/1993 | Hu et al. | |
| 5,212,122 A | 5/1993 | Pannhorst et al. | |
| 5,234,871 A | 8/1993 | Krashkevich | |
| 5,290,544 A | 3/1994 | Shimono et al. | 424/63 |
| 5,328,874 A | 7/1994 | Beall et al. | |
| 5,639,702 A | 6/1997 | Imashita et al. | 501/44 |
| 5,807,641 A | 9/1998 | Oku et al. | 428/701 |
| 5,834,008 A | 11/1998 | Greenspan et al. | 424/443 |
| 6,074,984 A | 6/2000 | Demmel et al. | 502/439 |
| 6,123,743 A | 9/2000 | Carman et al. | 51/307 |
| 6,143,318 A | 11/2000 | Gilchrist et al. | 424/446 |
| 6,245,732 B1 | 6/2001 | Gallon | 510/507 |
| 6,360,562 B1* | 3/2002 | Kodas et al. | 65/21.1 |
| 6,593,260 B2 | 7/2003 | Nomura | |
| 6,831,028 B1 | 12/2004 | Ishii et al. | |
| 6,846,760 B2 | 1/2005 | Siebers et al. | |
| 2001/0006987 A1 | 7/2001 | Nomura | |
| 2001/0023156 A1 | 9/2001 | Nomura | |
| 2002/0001604 A1 | 1/2002 | Shigeru et al. | |
| 2002/0086039 A1 | 7/2002 | Lee et al. | 424/401 |
| 2003/0129413 A1 | 7/2003 | Greiner et al. | |
| 2004/0137075 A1 | 7/2004 | Fechner et al. | 424/601 |
| 2004/0166172 A1 | 8/2004 | Rosati et al. | 424/601 |

(Continued)

FOREIGN PATENT DOCUMENTS

CN    1323527    11/2001

(Continued)

OTHER PUBLICATIONS

U.S. Patent Application entitled Antimicrobial, Anti-Inflammatory, Wound-Healing and Disinfecting Glass and Use Thereof filed on Feb. 19, 2004.

*Primary Examiner*—Johann R Richter
*Assistant Examiner*—James H. Alstrum-Acevedo
(74) *Attorney, Agent, or Firm*—Baker & Daniels LLP

(57) ABSTRACT

The invention relates to an anti-inflammatory, wound-healing glass powder, whereby the glass of the glass powder comprises the following components: 20-80 wt. % $SiO_2$, 0-40 wt. % $Na_2O$, 0-40 wt. % $K_2O$, 0-40 wt. % $Li_2O$, 0-40 wt. % $CaO$, 0-40 wt. % $MgO$, 0-40 wt. % $Al_2O_3$, 0-1 wt. % $P_2O_5$, 0-40 wt. % $B_2O_3$ and 0-10 wt. % $ZnO$.

32 Claims, 1 Drawing Sheet

U.S. PATENT DOCUMENTS

| | | | |
|---|---|---|---|
| 2005/0064193 A1 | 3/2005 | Fechner et al. | 428/406 |
| 2005/0069592 A1 | 3/2005 | Fechner et al. | |
| 2005/0119105 A1 | 6/2005 | Zimmer et al. | 501/32 |
| 2005/0176573 A1 | 8/2005 | Thoma et al. | |
| 2005/0233888 A1 | 10/2005 | Seneschal et al. | |
| 2006/0142413 A1 | 6/2006 | Zimmer et al. | |
| 2006/0166806 A1 | 7/2006 | Fechner et al. | |
| 2007/0122356 A1 | 5/2007 | Kessler et al. | |

FOREIGN PATENT DOCUMENTS

| | | | |
|---|---|---|---|
| CN | 1379146 | | 11/2002 |
| DE | 2800145 | | 9/1978 |
| DE | 3939831 | | 6/1990 |
| DE | 195 03 167 | | 8/1996 |
| EP | 0 141 580 | | 5/1985 |
| EP | 425927 | | 5/1991 |
| EP | 0 648 713 | | 4/1995 |
| EP | 0 773 196 | | 5/1997 |
| EP | 0921105 | | 6/1999 |
| EP | 1 116 698 | | 7/2001 |
| EP | 1 116 700 | | 7/2001 |
| EP | 1 270 527 | | 1/2003 |
| EP | 1 449 816 | | 8/2004 |
| GB | 1 294 337 | | 10/1972 |
| GB | 1 316 160 | | 5/1973 |
| GB | 2 178 422 | | 2/1987 |
| JP | 61-133813 | | 6/1986 |
| JP | 61186248 | * | 8/1986 |
| JP | 3-146436 | | 6/1991 |
| JP | 4-338129 | | 11/1992 |
| JP | 07026635 | | 1/1995 |
| JP | 7-048142 | | 2/1995 |
| JP | 7-291654 | | 11/1995 |
| JP | 8-48539 | | 2/1996 |
| JP | 8-175843 | | 7/1996 |
| JP | 8-217492 | | 8/1996 |
| JP | 8-245240 | | 9/1996 |
| JP | 10-059788 | | 3/1998 |
| JP | 10-101364 | | 4/1998 |
| JP | 10-158037 | | 6/1998 |
| JP | 10-218637 | | 8/1998 |
| JP | 10-231187 | | 9/1998 |
| JP | 11-029343 | | 2/1999 |
| JP | 11029343 | * | 2/1999 |
| JP | 11-060277 | | 3/1999 |
| JP | 11-209143 | | 8/1999 |
| JP | 11-228173 | | 8/1999 |
| JP | 11-278866 | | 10/1999 |
| JP | 11-319042 | | 11/1999 |
| JP | 2000-053451 | | 2/2000 |
| JP | 2000-191339 | | 7/2000 |
| JP | 2000-203876 | | 7/2000 |
| JP | 2000-264674 | | 9/2000 |
| JP | 2000-327369 | | 11/2000 |
| JP | 2001-026466 | | 1/2001 |
| JP | 2001-048595 | | 2/2001 |
| JP | 2001-247333 | | 9/2001 |
| JP | 2001-247334 | | 9/2001 |
| JP | 2001-247335 | | 9/2001 |
| JP | 2001-247336 | | 9/2001 |
| JP | 2001-247337 | | 9/2001 |
| JP | 2002-012442 | | 1/2002 |
| JP | 2003-206139 | | 7/2003 |
| WO | WO96/21628 | | 7/1996 |
| WO | WO 97/27148 | | 7/1997 |
| WO | 98/44965 | | 10/1998 |
| WO | WO00/15167 | | 3/2000 |
| WO | WO 00/38552 | | 7/2000 |
| WO | 00/49996 | | 8/2000 |
| WO | WO00/66086 | | 11/2000 |
| WO | WO00/76486 | | 12/2000 |
| WO | 01/03650 | | 1/2001 |
| WO | 01/72262 | | 10/2001 |
| WO | 02/28792 | | 4/2002 |
| WO | 03/018495 | | 3/2003 |
| WO | 03/018496 | | 3/2003 |
| WO | 03/018498 | | 3/2003 |
| WO | 03/018499 | | 3/2003 |
| WO | 03/062163 | | 7/2003 |
| WO | 2004/076369 | | 9/2004 |
| WO | 2004/076370 | | 9/2004 |
| WO | 2004/076371 | | 9/2004 |

* cited by examiner

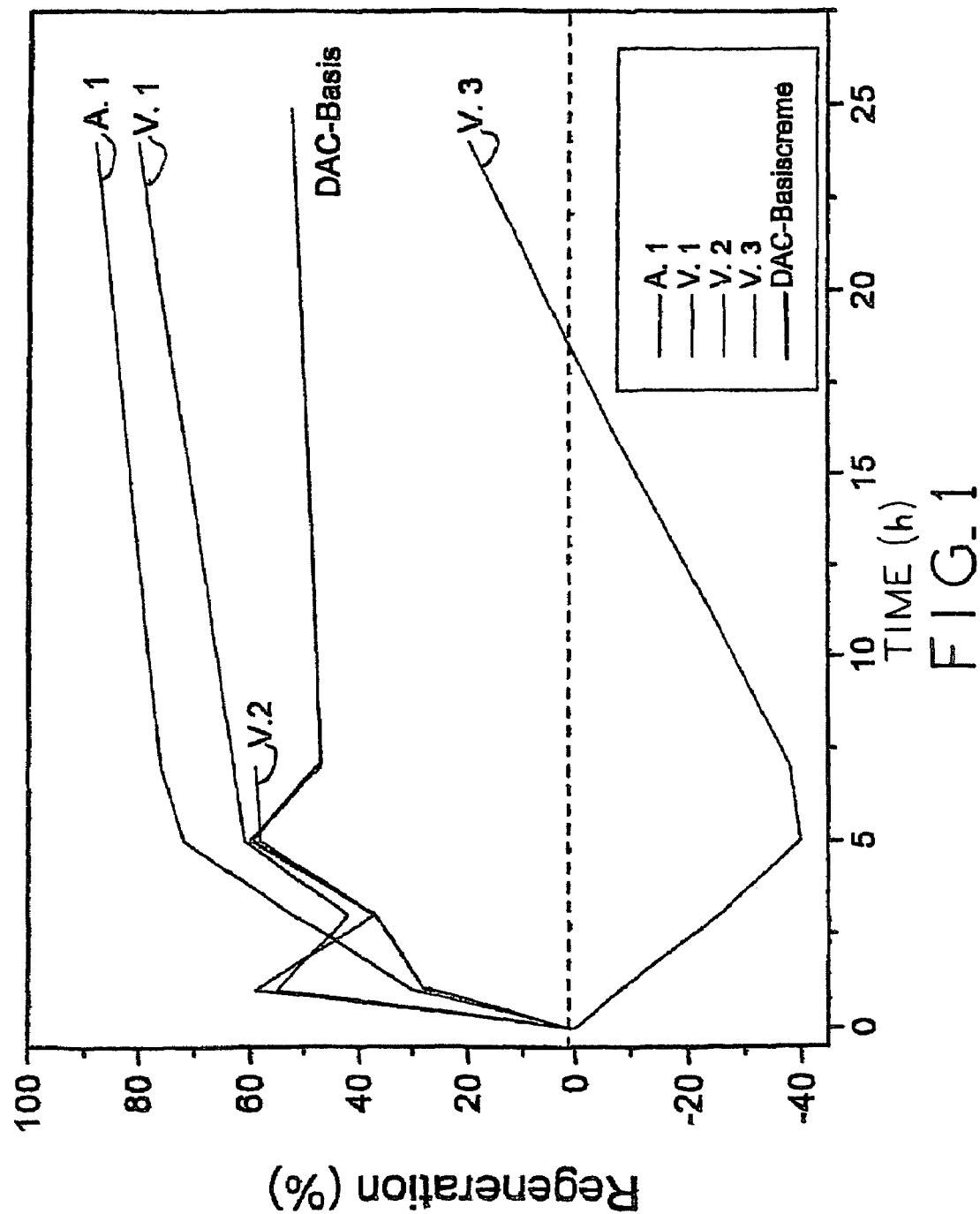

ANTIMICROBIAL, ANTI-INFLAMMATORY, WOUND-HEALING GLASS POWDER AND USE THEREOF

The invention relates to an antimicrobial, anti-inflammatory, wound-healing glass powder.

Anti-inflammatory wound-healing glass powders are known from the following publications:
U.S. Pat. No. 5,834,008
WO 0015167
WO 0066086

The anti-inflammatory and wound-healing glasses or glass powders made from such glasses comprise as per the state of the art all bioactive glasses.

In the case of the bioactive glasses known from the aforementioned publications with anti-inflammatory effect the bioactive glass exhibits a significant phosphorus content>1 wt. %.

The essential properties of bioactive glass are known to the person skilled in the art and are described, for example, in U.S. Pat. No. 5,074,916. According to said document, bioactive glass differs from conventional calcium-sodium-silicate glasses in that it binds living tissue.

Bioactive glass denotes a glass that forms a fixed bond with body tissue, whereby a hydroxylapatite layer is formed.

The drawback to bioactive glasses is the high phosphorus content, which results in production problems during the smelting of the glasses.

In addition, because of their low hydrolytic resistance bioactive glasses are only suitable to a very restricted degree for grinding in aqueous media.

Thus it is the object of the invention to make available an anti-inflammatory and wound-healing glass powder which, as opposed to bioactive glasses or glass powders composed of such glasses, is easier to produce, toxicologically safe and is not harmful to the environment.

By glass powder a powder comprising a multitude of glass particles of random shape is understood, including glass fibers as well, for example a glass bead with particle size of <1 mm preferably <500 μm or a glass fiber with a diameter of <1 mm preferably <μ500 m.

In addition the glass powders should comprise glass ingredients which exhibit a skin-soothing, anti-inflammatory and wound-healing effect on skin irritations, acute as well as chronic wounds or inflammations, are however toxicologically safe in contact with human beings and in particular are also suitable for consumption.

In accordance with the invention the task is solved by means of an anti-inflammatory and wound-healing glass powder as per one of claims 1, 4 or 7. Preferably the glass of the glass powder can comprise 20-80 wt. % $SiO_2$, 0-40 wt. % $Na_2O$, 0-40 wt. % $K_2O$, 0-40 wt. % $Li_2O$, 0-40 wt. % CaO, 0-40 wt. % MgO, 0-40 wt. % $Al_2O_3$, 0-1 wt. % $P_2O_5$, 0-40 wt. % $B_2O_3$. Preferably the glass can also contain 0-30 wt. % $XF_y$, whereby X can be Li, Na, K, Be, Mg, Ca and y=1 or y=2. Preferably the amount $Na_2O+K_2O+Li_2O$ 5 to 50 wt. %. Alternatively the amount+CaO+MgO can be 5 to 50 wt. %.

The glass powder of the invention can be produced on a commercial scale with standard methods, since the glass composition can be smelted on a commercial scale.

The glass powder of the invention can be added to products. On the basis of their hydrolytic resistance the glass ingredients can also be ground into glass powders in aqueous grinding media In addition to the anti-inflammatory effect, the glass powders also exhibit antimicrobial properties.

The glasses which are ground into glass powders can be produced quite purely. The glass powders are then toxicologically safe as well as suitable for consumption. For example, the maximum concentration in the field of cosmetic products preferably for Pb amounts to <20 ppm, for Cd is <5 ppm, As<5 ppm, Sb<10 ppm, Hg<1 ppm, Ni<10 ppm.

As a result of the additional antimicrobial effect a conservation of products themselves can be achieved or an antimicrobial effect toward the outside can be attained. Fields of application for this are for example cosmetic products, deodorant products, foods, paints, lacquers, plasters, paper hygiene products, medicinal products and cleansers.

For certain fields of application added amounts of heavy metals such as Ag, Cu, Zn are advantageous for achieving a synergistically strengthened antimicrobial and anti-inflammatory effect.

Skin irritations play a significant role in the field of cosmetics. For this reason it is advantageous if the anti-inflammatory and wound-healing glass powder is particularly eudermic.

One particular advantage of the invention's glass powder is the fact that it comprises a glass that due to the fusion and heat forming behavior is suitable for being produced in corresponding commercial plants.

Since the process temperatures or the viscosity of the glass is low, cost-beneficial materials can be employed in fusion and heat forming.

Along with production by means of a smelting procedure, alternative production methods via the sol-gel or reaction sintering route are also conceivable.

Surprisingly, the glass powders of the invention comprising the specified glass composition have an anti-inflammatory and wound-healing effect that can be extremely strong. The lower the mean particle size of the glass powder, the higher the anti-inflammatory and wound-healing effect due to the increase of the reactive surface of the glass.

Surprisingly, this anti-inflammatory and wound-healing property is also found in glasses comprising glass powders which as semi-finished products possess a relatively high hydrolytic resistance. With low particle size and with a large surface, however a drastic reactivity increase shows, as a result of which through the following described ion exchange an anti-inflammatory and wound-healing effect occurs.

In the case of the glass powders of the invention, alkalis of the glass are exchanged by $H^+$ ions of the aqueous medium by means of reactions on the surface of the glass. The anti-inflammatory and wound-healing effect is based, among other things, on a release of ions as well as on surface effects of the particles such as for example the surface charge as well as the antimicrobial effect of the glass powders on germs.

Glass powders with ion-exchangeable glasses in accordance with the invention have an anti-inflammatory and wound-healing effect in aqueous media by means of ionic exchange between a metallic ion, such as for example an alkaline or alkaline earth metallic ion and the $H^+$ ions of the aqueous solution as well as by means of ion-caused impairment of the cell growth (osmotic pressure, influence of metabolic processes of the cells). The ground glass powders with particles of slighter particle size and greater surface show a drastic increase in reactivity, as a result of which, by means of the previously described ionic exchange, a strong anti-inflammatory and wound-healing effect occurs. The reason for this is the exchange of ions which can have an anti-inflammatory effect, for example of potassium. The anti-inflammatory effect of the glass powders is surprising for the person skilled in the art, since the glass compositions in an unground state are largely inert. By means of the grinding up of such a largely inert composition one can achieve a release of ions in the ground up glass powder such as for example K, which have an anti-inflammatory effect on the epidermis. Such anti-inflammatory properties have always been attributed in the state of the art to powders made of reactive glasses with a phosphorus content greater than 1 wt. %, since the formation of hydroxylapatite layers has always been considered to be necessary for the bioactive and anti-inflammatory effect.

With the help of grinding processes the glass ingredients can be ground into glass powder with particle sizes <100 μm. Particle sizes <50 μm or 20 μm have proved to be expedient. Particle sizes <10 μm as well as less than 5 μm are especially suitable. Particle sizes <2 μm and less than <1 μm have turned out to be ideal.

The grinding process can be performed both dry as well as with aqueous and non-aqueous grinding media.

Mixtures of different glass powders from the composition range with variable ingredients and particle sizes are possible, in order to combine specific effects.

pH values ranging from one to 13 are attained, depending on the particle size, concentration and the composition of the powder.

Mixtures of glass powders with variable ingredients and particle sizes can be synergistically combined for the setting of special properties of the individual glass powders. For example it is possible to control the anti-inflammatory and wound-healing effect of the glass powder by means of the particle size.

The glass of the glass powder contains $SiO_2$ as a network-forming ion, preferably between 35 to 80 wt. %. With lower concentrations the hydrolytic resistance is greatly diminished, so that the grinding in aqueous media is no longer guaranteed without significant dissolution of the glass.

$Na_2O$ is employed as a fluxing agent in the melting of the glass. At concentrations of less than 5% the melting behavior is negatively influenced. What is more, the necessary mechanism of the ionic exchange is no longer sufficient to achieve an anti-inflammatory and wound-healing effect. In the case of $Na_2O$ concentrations greater than 30 wt. % a deterioration of the chemical resistance or hydrolytic resistance is to be observed, particularly in combination with a decrease of the $SiO_2$ content.

Alkaline and alkaline earth oxides can be added in order to increase the ionic exchange and thus amplify the anti-inflammatory and wound-healing effect.

The quantity of $Al_2O_3$ can be added up to a maximum of 8 wt. % to increase the chemical resistance of the crystallization stability as well as for controlling the antimicrobial effect $B_2O_3$ acts as a network-forming ion and can also be used to for controlling the anti-inflammatory and wound-healing effect.

AnO is an essential component for the hot forming properties of the glass. It improves the crystallization stability and increases the surface tension. Moreover it can support the anti-inflammatory and wound-healing effect. At slight $SiO_2$ contents it increases the crystallization stability. To achieve an anti-inflammatory and wound-healing effect up to 8 wt. % ZnO can be included. A preferred implementation contains <4 wt. % ZnO or <2 wt. %. Implementations with <1 wt. % or 0.5 wt. % or <0.1 wt. % are especially preferred.

AgO, CuO can be added as active additives to amplify the anti-inflammatory and wound-healing effect of the base glass.

The glass of the invention does not cause any skin-irritating effects.

By means of a combination of the pH effect and the Ag, Cu or Zn decrease, a considerable increase of the anti-inflammatory and wound-healing effect as well as the additional antimicrobial effect can be achieved, which significantly exceeds the sum of the individual effects. In the process the concentration of Ag, Cu, Zn ions released in the product can lie significantly below 1 ppm.

The introduction of Ag, Cu, Zn can occur during the melting through corresponding salts or by means of ionic exchange of the glass after the melting.

To achieve color effects single or even multiple coloring components such as for example Fe2O3, CoO, CuO, V2O5, Cr2O5 can be added to the glass in a total concentration less than 4 wt. %, preferably less than 1 wt. %.

Glass powders with glasses lying within the claimed composition range fulfill all requirements with regard to usage in the areas of paper hygiene, cosmetics, paints, lacquers, plasters, medicinal products, cosmetic applications, as well as use in deodorant products, antiperspirants as well as in products for the treatment of skin irritations, acute and chronic wounds.

One property of the glass powder is the surprisingly proven skin tolerance, which is also given in the case of high concentrations with high pH values.

The glass powder can be used in any suitable form. Mixtures of different glass powders from the composition range with different ingredients are also possible. Mixture with different glass powders is also possible, in order to combine specific effects.

Components such as fluorine can, depending on the application area, be added to the glass up to concentrations of 5 wt. % in total.

The glass described in this invention from which glass powder of the invention is obtained by grinding is either not water-soluble, or is very difficult to dissolve in water. The glass powder acts primarily by means of ionic exchange or ion loss, which is combined with a surface reaction, pH increase and metallic ion release.

Surprisingly the glass powders in accordance with the invention show a higher anti-inflammatory and wound-healing effect than the group of bioactive glasses which were described in the state of the art or glass powders that were produced from such glasses.

In the following the invention will be described using the embodiments and figures.

BRIEF DESCRIPTION OF THE DRAWING

The FIGURE shows the following:
FIG. 1 shows the regeneration of the barrier function of the epidermis after preliminary lesion.

EMBODIMENTS

Out of raw materials the glass was melted in a quartz glass crucible, and then processed into ribbons. The ribbons were further processed by means of dry grinding into powder with a particle size d50=4 μm.

Table 2 specifies the compositions and properties of glasses that can be ground into the glass powders of the invention. The compositions refer to synthetic values in wt. % on an oxide basis.

TABLE 1

|  | V.1 | V.2 | V.3 |
|---|---|---|---|
| $SiO_2$ | 45.0 | 58.2 | 35.0 |
| $Al_2O_3$ | | | |

TABLE 1-continued

|  | V.1 | V.2 | V.3 |
|---|---|---|---|
| CaO | 24.5 | 32.6 | 29.5 |
| MgO |  |  |  |
| Fe$_2$O$_3$ |  |  |  |
| Na$_2$O | 24.5 |  | 29.5 |
| K$_2$O |  |  |  |
| P$_2$O$_5$ | 6.0 | 9.2 | 6.0 |

TABLE 2

|  | Embodiment 1 | Embodiment 2 | Embodiment 3 | Embodiment 4 | Embodiment 5 | Embodiment 6 | Embodiment 7 |
|---|---|---|---|---|---|---|---|
| SiO$_2$ | 71.2 | 45.0 | 72.0 | 60.0 | 48.0 | 45.0 | 45.0 |
| B$_2$O$_3$ |  |  |  |  |  |  | 10.0 |
| Al$_2$O$_3$ | 0.35 |  |  |  |  |  |  |
| P$_2$O$_5$ |  |  |  |  |  | 1.0 |  |
| CaO | 9.9 | 24.5 | 9.6 | 20.0 | 20.0 | 27.5 | 25.0 |
| MgO | 4.2 |  | 4.0 |  | 10.0 |  |  |
| Fe$_2$O$_3$ | 0.1 |  |  |  |  |  |  |
| Li$_2$O |  |  |  |  | 2.0 |  |  |
| Na$_2$O | 14.2 | 30.5 | 14.4 | 20.0 | 10.0 | 27.5 | 15.0 |
| K$_2$O | 0.05 |  |  |  | 10.0 |  | 5.0 |

Table 1 shows comparison examples of bioactive glasses V1, V2, and V3.

Table 2 shows embodiments A1 through A7.

Particularly easy to produce and commercially available, because they can be melted in commercial plants, are glasses that comprise the following components, whereby the specifications are in wt. % on an oxide basis:

SiO$_2$: 68-75 wt. %, Na$_2$O: 10-20 wt. %, Al$_2$O$_3$: 0-3 wt. %, CaO: 5-15 wt. %, MgO: 0-10 wt. %. Such glasses exhibit an anti-inflammatory and wound-healing effect after grinding. This is surprising for the person skilled in the art, since glasses with a phosphorus content less than 1 wt. % with reference to oxide basis, for example soda-lime glasses are largely non-reactive as glass. Only phosphorus-containing glasses with a phosphorus content >1 wt. % had an anti-inflammatory effect attributed to them, since these glasses are considered to be very reactive.

All glasses, in particular the suitable glasses in the above specified composition can exhibit trace elements and/or conventional refining agents in conventional quantities. Trace elements are for example impurities contained in glass such as Fe$_2$O$_3$ or K$_2$O; conventional refining agents As$_2$O$_3$, Sb$_2$O$_3$.

Studies on mice show an anti-inflammatory and wound-healing effect that is superior to that of bioactive glasses. Trials were performed with one mouse each at three measuring points. The active substances examined as glass powder A.1, V.1, V.2, and V.3 were applied to a quantity of 10 wt. % in a DAC base cream. For comparison with the DAC cream provided with an active substance, a DAC base cream without active substance was also applied.

FIG. 1 shows the time course of the repair of a surface wound, i.e. the regeneration of the barrier function of the epidermis, measured through the transepidermal water loss. The surface wound was obtained by means of a preliminary lesion with tape stripping. By tape stripping, the lesion of the top skin layers by means of the applying and removing of tape strips is understood.

In FIG. 1 it can be recognized that the regeneration of the barrier function of the skin after 24 hours with a glass powder with the invention's glass composition is approximately 10% better than with the bioactive glass powder V.1. The bioactive glass powders V.2 and V.3 as well as the DAC cream without an active substance as reference samples show an even significantly lower regeneration of the barrier function. The comparative experiments show clearly the anti-inflammatory, wound-healing effect of the invention's glass powders with the specified glass composition, which is superior to that of the bioactive glass powders. Furthermore, the glass powders in accordance with the invention also exhibit an antimicrobial effect. This is specified as per Europ. Pharmakopoe ($3^{rd}$ Edition) for the embodiment A1 with a particle size of 4 μm in Table 3.

TABLE 3

|  | E. coli | P. eruginosa | S. aureus | C. albicans | A. niger |
|---|---|---|---|---|---|
| Start | 290000 | 270000 | 250000 | 300000 | 250000 |
| 2 days | 900 | 1800 | 800 | <100 | 2000 |
| 7 days | <100 | 200 | <100 | 0 | 2000 |
| 14 days | 0 | 0 | 0 | 0 | 0 |
| 21 days | 0 | 0 | 0 | 0 | 0 |
| 28 days | 0 | 0 | 0 | 0 | 0 |

The anti-inflammatory and wound-healing acting glass powders can be applied as food additive, in cosmetic products and deodorant products, in particular for reduction of skin irritations, but not restricted to said reduction of skin irritations, in medicinal products, in particular products for wound care and treatment, plastics and polymers, paper hygiene, in paints, lacquers as well as in cleansers.

The invention claimed is:

1. A cosmetic product, comprising:
a glass powder, whereby the glass of the glass powder comprises the following components in wt. % on an oxide basis:
20-48 wt. % SiO$_2$
0-40 wt. % Na$_2$O
0-40 wt. % K$_2$O
0-40 wt. % Li$_2$O
0-40 wt. % CaO
0-40 wt. % MgO
0-8 wt. % Al$_2$O$_3$
0 wt. % P$_2$O$_5$
0-40 wt. % B$_2$O$_3$
0-10 wt. % ZnO
whereby the total Na$_2$O+K$_2$O+Li$_2$O+CaO+MgO amounts to 15 to 80 wt. %, the amount of Pb is <20 ppm, the glass of the glass powder is free from Ag, and the average size of the glass particles of the glass powder is <20 μm.

2. The cosmetic product according to claim 1, whereby the total $Na_2O+K_2O+Li_2O$ amounts to 5 to 50 wt. %.

3. The cosmetic product according to claim 1, whereby the total CaO+MgO amounts to 5 to 50 wt. %.

4. The cosmetic product according to claim 1, whereby the glass of the glass powder further comprises 0-30 wt. % of a fluorine-containing compound of the formula $XF_y$, whereby X is an element selected from the group consisting of Li, Na, K, Be, Mg, and Ca and y=1 or y=2.

5. The cosmetic product according to claim 1, whereby the glass of the glass powder further comprises 0-10 wt. % of a fluorine-containing compound of the formula $XF_y$, whereby X is an element selected from the group consisting of Li, Na, K, Be, Mg, and Ca and y=1 or y=2.

6. The cosmetic product according to claim 1, wherein the glass of the glass powder additionally comprises at least one ion selected from the group consisting of Cu and Zn ions.

7. The cosmetic product according to claim 1, wherein the glass of the glass powder is free of Cu.

8. The cosmetic product according to claim 1, wherein the average size of the particle of the glass powder is <10 μm.

9. The cosmetic product according to claim 1, wherein the average size of the glass particle is <5 μm.

10. The cosmetic product according to claim 1, wherein the average size of the glass particle of the glass powder is <1 μm.

11. The cosmetic product according to claim 1, wherein the $Al_2O_3$ content is 0-3 wt. %.

12. A method for production of the cosmetic product according to claim 1, comprising the following steps:
 (a) smelting the glass;
 (b) processing the glass; and
 (c) grinding the glass into glass powder.

13. A deodorant product, comprising:
 a glass powder, whereby the glass of the glass powder comprises the following components in wt. % on an oxide basis:
 20-48 wt. % $SiO_2$
 0-40 wt. % $Na_2O$
 0-40 wt. % $K_2O$
 0-40 wt. % $Li_2O$
 0-40 wt. % CaO
 0-40 wt. % MgO
 0-8 wt. % $Al_2O_3$
 0 wt. % $P_2O_5$
 0-40 wt. % $B_2O_3$
 0-10 wt. % ZnO
whereby the total $Na_2O+K_2O+Li_2O+CaO+MgO$ amounts to 15 to 80 wt. %, , the amount of Pb is <20 ppm, the glass of the glass powder is free from Ag, and the average size of the glass particles of the glass powder is <20 μm.

14. The deodorant product according to claim 13, wherein the $Al_2O_3$ content is 0-3 wt. %.

15. A medicinal product, comprising:
 a glass powder, whereby the glass of the glass powder comprises the following components in wt. % on an oxide basis:
 20-48 wt. % $SiO_2$
 0-40 wt. % $Na_2O$
 0-40 wt. % $K_2O$
 0-40 wt. % $Li_2O$
 0-40 wt. % CaO
 0-40 wt. % MgO
 0-8 wt. % $Al_2O_3$
 0 wt. % $P_2O_5$
 0-40 wt. % $B_2O_3$
 0-10 wt. % ZnO
whereby the total $Na_2O+K_2O+Li_2O+CaO+MgO$ amounts to 15 to 80 wt. %, , the amount of Pb is <20 ppm, the glass of the glass powder is free from Ag, and the average size of the glass particles of the glass powder is <20 μm.

16. The medicinal product according to claim 15, whereby the total $Na_2O+K_2O+Li_2O$ amounts to 5 to 50 wt. %.

17. The medicinal product according to claim 15, whereby the total CaO+MgO amounts to 5 to 50 wt. %.

18. The medicinal product according to claim 15, whereby the glass of the glass powder further comprises 0-30 wt. % of a fluorine-containing compound of the formula $XF_y$, whereby X is an element selected from the group consisting of Li, Na, K, Be, Mg, and Ca and y=1 or y=2.

19. The medicinal product according to claim 15, whereby the glass of the glass powder further comprises 0-10 wt. % of a fluorine-containing compound of the formula $XF_y$, whereby X is an element selected from the group consisting of Li, Na, K, Be, Mg, and Ca and y=1 or y=2.

20. The medicinal product according to claim 15, wherein the glass of the glass powder additionally comprises at least one ion selected from the group consisting of Cu and Zn ions.

21. The medicinal product according to claim 15, wherein the glass of the glass powder is free of Cu.

22. The medicinal product according to claim 15, wherein the average size of the particle of the glass powder is <10 μm.

23. The medicinal product according to claim 15, wherein the average size of the glass particle is <5 μm.

24. The medicinal product according to claim 15, wherein the average size of the glass particle of the glass powder is <1 μm.

25. The medicinal product according to claim 15, wherein the $Al_2O_3$ content is 0-3 wt %.

26. A method for production of the medicinal product according to claim 15, comprising the following steps:
 (a) smelting the glass;
 (b) processing the glass; and
 (c) grinding the glass into glass powder.

27. An antiperspirant, comprising:
 a glass powder, whereby the glass of the glass powder comprises the following components in wt. % on an oxide basis:
 20-48 wt. % $SiO_2$
 0-40 wt. % $Na_2O$
 0-40 wt. % $K_2O$
 040 wt. % $Li_2O$
 0-40 wt. % CaO
 0-40 wt. % MgO
 0-8 wt. % $Al_2O_3$
 0 wt. % $P_2O_5$
 0-40 wt. % $B_2O_3$
 0-10 wt. % ZnO
whereby the total $Na_2O+K_2O+Li_2O+CaO+MgO$ amounts to 15 to 80 wt. %, ,the amount of Pb is <20 ppm, the glass of the glass powder is free from Ag, and the average size of the glass particles of the glass powder is <20 μm.

28. The antiperspirant according to claim 27, wherein the $Al_2O_3$ content is 0-3 wt. %.

29. A product for the treatment of skin irritations, acute and chronic wounds, comprising:
 a glass powder, whereby the glass of the glass powder comprises the following components in wt. % on an oxide basis:
 20-48 wt. % $SiO_2$
 0-40 wt. % $Na_2O$
 0-40 wt. % $K_2O$
 0-40 wt. % $Li_2O$
 0-40 wt. % CaO 0-40 wt. % MgO
0-8 wt. % $Al_2O_3$
0 wt. % $P_2O_5$
0-40 wt. % $B_2O_3$
0-10 wt. % ZnO whereby the total $Na_2O+K_2O+Li_2O+CaO+MgO$ amounts to 15 to 80 wt. %, , the amount of Pb is <20 ppm, the glass of the glass powder is free from Ag, and the average size of the glass particles of the glass powder is <20 μm.

30. The product for the treatment of skin irritations according to claim 29, wherein the $Al_2O_3$ content is 0-3 wt. %.

31. A personal care product, comprising a glass powder, whereby the glass of the glass powder comprises the following components in wt. % on an oxide basis:

20-48 wt. % $SiO_2$
0-40 wt. % $Na_2O$
0-40 wt. % $K_2O$
0-40 wt. % $Li_2O$
0-40 wt. % CaO
0-40 wt. % MgO
0-8 wt. % $Al_2O_3$
0 wt. % $P_2O_5$
0-40 wt. % $B_2O_3$
0-10 wt. % ZnO whereby the total $Na_2O+K_2O+Li_2O+CaO+MgO$ amounts to 15 to 80 wt. %, , the amount of Pb is <20 ppm, the glass of the glass powder is free from Ag, and the average size of the glass particles of the glass powder is <20 μm.

32. The personal care product according to claim 31, wherein the $Al_2O_3$ content is 0-3 wt. %.

* * * * *